US006140069A

United States Patent [19]
Wardlaw

[11] Patent Number: 6,140,069
[45] Date of Patent: *Oct. 31, 2000

[54] METHOD FOR DETERMINING ANTIBIOTIC SENSITIVITY OF BACTERIA

[75] Inventor: Stephen C. Wardlaw, Old Saybrook, Conn.

[73] Assignees: Wardlaw Partners, LL.P., Lyme; Robert A. Levine, Guilford, both of Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/255,681

[22] Filed: Feb. 23, 1999

Related U.S. Application Data
[60] Provisional application No. 60/077,217, Mar. 7, 1998.
[51] Int. Cl.[7] .............................. C12Q 1/18; C12Q 1/00; C12Q 1/02; C12Q 1/24
[52] U.S. Cl. ............................ 435/32; 435/4; 435/283.1; 435/29; 435/30
[58] Field of Search .............................. 435/32, 4, 283.1, 435/29, 30

[56] References Cited

U.S. PATENT DOCUMENTS

| | | | |
|---|---|---|---|
| 4,054,490 | 10/1977 | Vesterberg | 195/103.5 K |
| 4,204,045 | 5/1980 | Kjellander et al. | 435/301 |
| 4,514,495 | 4/1985 | Schalkowsky et al. | 435/32 |
| 4,778,758 | 10/1988 | Ericsson et al. | 435/32 |
| 4,790,640 | 12/1988 | Nason | 350/534 |
| 4,950,455 | 8/1990 | Smith | 422/56 |
| 5,028,529 | 7/1991 | Ericsson et al. | 435/30 |
| 5,164,301 | 11/1992 | Thompson et al. | 435/29 |
| 5,206,151 | 4/1993 | Robertson | 435/32 |
| 5,246,837 | 9/1993 | Schalkowsky | 435/29 |
| 5,427,959 | 6/1995 | Nishimura et al. | 436/534 |
| 5,501,959 | 3/1996 | Lancaster et al. | 435/32 |
| 5,547,849 | 8/1996 | Baer et al. | 435/7.24 |
| 5,563,043 | 10/1996 | Schalkowsky et al. | 435/32 |
| 5,639,632 | 6/1997 | Ericsson et al. | 435/32 |
| 5,702,684 | 12/1997 | McCoy et al. | 424/10.3 |

OTHER PUBLICATIONS

Beven et al, Current Microbiology, vol. 33, pp 317–322, 1996.

Majtan et al, Folia Microbiologica (Abstract), vol. 42, No. 4, p 327–332, 1997.

*Primary Examiner*—Louise N. Leary

[57] ABSTRACT

A method and apparatus for determining the minimum inhibitory concentration of an antibiotic for a target microorganism is provided. The method includes the steps of: (a) providing a microorganism growth medium; (b) providing a sensible reagent, which includes an antibiotic mixed with a marker, the marker having a signal with a magnitude proportional to the marker's concentration; (c) incorporating the reagent into the growth medium, in a manner that creates a gradient of concentrations of the antibiotic and marker within the growth medium; (c) inoculating the growth medium with the target microorganism; (d) incubating the inoculated growth medium for a period of time sufficient for the target microorganism to grow a detectable amount on a first section of growth medium; (e) determining a growth boundary between the first section of growth medium having detectable target microorganism growth and a second section having substantially no detectable target microorganism growth; (f) measuring the signal magnitude at the growth boundary; and (g) determining a minimum inhibitory concentration of the antibiotic using the measured signal magnitude.

20 Claims, 1 Drawing Sheet

METHOD FOR DETERMINING ANTIBIOTIC SENSITIVITY OF BACTERIA

This application claims the benefit of U.S. Provisional Application No. 60/077,217, filed Mar. 7, 1998.

BACKGROUND OF THE INVENTION

1. Technical Field

The present invention relates to methods and apparatus for determining a microorganism's sensitivity to an antibiotic in general, and to methods and apparatus for determining the minimum inhibitory concentration of an antibiotic relative to a microorganism in particular.

2. Background Information

The determination of the minimum inhibitory concentration (MIC) of an antibiotic is an essential laboratory test to determine the sensitivity of a microorganism, usually a bacterium, to specific antibiotics. The MIC refers to the minimum concentration of an antibiotic necessary to prevent the microorganism from growing. The type and dose of antibiotics is often predicated upon this type of test, making rapid and accurate results critical to both patient care and cost-effective treatment. Antibiotic sensitivity testing is most commonly performed using the qualitative Kirby-Bauer plate method, but for a quantitative MIC analysis, the tube dilution is most commonly used.

The Kirby-Bauer test utilizes a plate covered with a uniform layer of microbiological growth medium specifically formulated for the test at hand. A number of disks are placed on the layer of growth medium, each containing a specific concentration of an antibiotic being evaluated. Bacteria grows on the medium forming a visible coating, except in the area (generally referred to as the "clear_zone") around those disks having sufficient antibiotic concentration to inhibit bacterial growth. The size of the clear zone surrounding a disk is indicative of the microorganism's sensitivity to the antibiotic contained in that particular disk; i.e., the larger the clear zone, the greater the microorganism's sensitivity to the antibiotic contained in the disk. The Kirby-Bauer test is popular because of its simplicity and its ability to evaluate multiple antibiotics at once. A disadvantage of the Kirby-Bauer test is that there are a number of variables which affect the antibiotic concentration at any given point in the growth medium, and thus do not allow a MIC to be calculated. Formulae have been published for calculating the approximate MIC based upon the clear zone size, but these formulae are rarely used and are considered to be approximations at best.

The tube dilution method involves placing an equal amount of target microorganism in a plurality of wells (referred to as "tubes") disposed in a platter, and adding different concentrations of an antibiotic to each tube. The lowest concentration of 5antibiotic in which the target microorganism will not grow determines the MIC for that particular microorganism. A disadvantage of the tube dilution method is that its accuracy depends on the step size in concentration change between tubes. A small step size yields greater accuracy, but may require an impractical number of tubes and effort. In addition, preparing accurate dilutions is an expensive process that increases in cost with the number of tubes. Hence, increasing the accuracy of this method can also increase the cost and time required.

An alternative means of performing a MIC determination is described in U.S. Pat. No. 4,778,758 and others, which involves the use of an "E-Strip", which is a strip that incorporates a precisely formed gradient of a single antibiotic. Calibration marks are disposed along a side of the strip, corresponding to the exact concentration of the antibiotic at that point. The strip is placed onto an inoculated Kirby-Bauer plate and after incubation a clear area will form contiguous with an area of microorganism growth, provided an antibiotic concentration within the gradient exceeds the MIC. The calibration markings corresponding to the border between the clear area and the growth area give the MIC value for the antibiotic being evaluated. Several disadvantages are associated with this method for determining a MIC of an antibiotic including, but not limited to: 1) the strip is difficult to manufacture and consequently expensive; 2) the size of the strip makes it impractical for concurrent multiple antibiotic tests in a single apparatus; and 3) the preparation must be read after a precise period of incubation to achieve optimum accuracy.

U.S. Pat. No. 5,702,684 discloses a method for monitoring antibiotic levels for determining when the antibiotics should be replenished in an industrial plumbing system using a fluorescent marker. That method, however, does not allow the determination of a MIC or any type of antibiotic sensitivity measurement.

What is needed is a method for determining the MIC of an antibiotic for a target microorganism, a method that can determine the MIC in a minimum amount of time, a method that provides an accurate MIC, a method that can simultaneously determine the MIC's of several antibiotics for a target microorganism, and a method that is cost effective.

DISCLOSURE OF THE INVENTION

It is, therefore, an object of the present invention to provide a method for determining the MIC of an antibiotic for a target microorganism that provides an accurate result in less time than it takes current known methods.

It is another object of the present invention to provide a method for determining the MIC's of several antibiotics for a target microorganism.

It is another object of the present invention to provide a method for determining the MIC of an antibiotic for a target microorganism that has utility in veterinary medicine.

According to the present invention, a method for determining the MIC of an antibiotic for a target microorganism is provided, comprising the steps of:

(a) providing a microorganism growth medium;

(b) providing a sensible reagent, which includes an antibiotic mixed with a marker having a signal with a magnitude which is proportional to the concentration of the marker, (c) incorporating the sensible reagent into the growth medium, in a manner that creates a gradient of antibiotic and marker concentrations within the growth medium;

(d) inoculating the growth medium with the target microorganism;

(e) incubating the inoculated growth medium for a period of time sufficient for the target microorganism to grow a detectable amount;

(f) determining a growth boundary between a section of the growth medium having detectable target microorganism growth and a section having substantially no detectable target microorganism; and (g) measuring the magnitude of the marker signal at the growth boundary; and (h) determining the minimum inhibitory concentration of the antibiotic using the measured magnitude of the marker signal.

An advantage of the present invention is that a method for determining the MIC of an antibiotic for a target microorganism is provided that gives accurate results in less time than it takes current known methods. The present invention uses a sensible reagent that includes a marker having a signal with a magnitude that is proportional to the concentration of the marker. The concentration of the marker within the reagent is proportional to the concentration of the antibiotic. The MIC of antibiotic at the growth boundary can therefore be determined by sensing the marker signal at the growth boundary. Accordingly, the exact MIC of antibiotic can be determined rather than an approximation, and can be determined without a multitude of time consuming dilution steps.

Another advantage of the present invention is that the MIC's of several antibiotics for a target microorganism can be determined concurrently using the present invention method. For example, a number of independent growth medium regions inoculated with a target microorganism can be plated in a single vessel, and a different antibiotic incorporated into each independent region. The remaining steps of the present invention method can then be applied to ascertain the MIC of the particular antibiotic incorporated within each growth medium region.

Another advantage of the present invention is that a cost effective method for determining the MIC of an antibiotic for a target microorganism is provided. The ability of the present invention method to provide accurate MIC information obviates the need for multiple expensive antibiotic dilutions as are required in the tube dilution method. A person of skill in the art will recognize that minimizing expensive medical laboratory time and laboratory assets make the present invention method considerably less expensive than presently available methods.

Another advantage of the present invention is that a method for determining the MIC of an antibiotic for a target microorganism is provided that has utility in veterinary medicine.

Another advantage of the present invention is that the effectiveness of a variety of antibiotics in various concentrations for a particular target microorganism can be readily determined. As a result, a caregiver considering an antibiotic application can make a better informed decision with respect to the type and effective dosage of an antibiotic, consequently benefiting the antibiotic recipient.

These and other objects, features and advantages of the present invention will become apparent in light of the detailed description of the best mode embodiment thereof, as illustrated in the accompanying drawings.

BEST MODE FOR CARRYING OUT THE INVENTION

Figure 1:
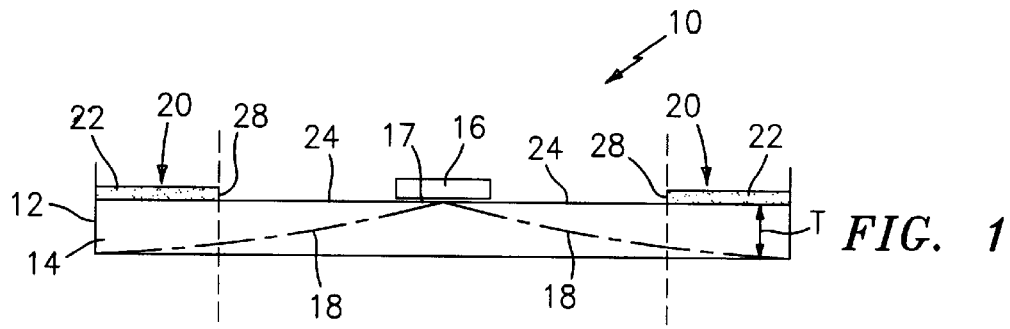
FIG. 1 shows a diagrammatic cross-section of a Kirby-Bauer plate type apparatus to illustrate the present invention method.

The present invention method for determining the minimum inhibitory concentration (MIC) of an antibiotic for a target microorganism includes the steps of providing a microorganism growth medium, an effective amount of target microorganism, and a sensible reagent. The growth medium must be capable of supporting the microorganism and may be a gel-type medium or a permeable solid growth medium. Dehydrated growth mediums that may be rehydrated during use are particularly favorable because they can be readily stored for extended periods of time. The target microorganism may consist of either first generation microbes taken, for example, from a urine sample, or a suspension of microbes taken, for example, from a colony grown on another growth medium. The target microorganism is typically a constituent within a liquid solution, although a diffusible gel bearing the target microorganism may be used alternatively. The liquid solution bearing the target microorganism facilitates the step of inoculating the growth medium with the target microorganism, particularly when a dehydrated growth medium is used.

The sensible reagent includes the antibiotic to be evaluated and a marker. In a first embodiment, sensible reagent contains an accurate quantity of the antibiotic to be evaluated mixed with a useful, but imprecisely measured, quantity of marker. In a second embodiment, the antibiotic to be evaluated and the marker of the reagent are mixed in known accurate proportion, and the overall quantity of the reagent may vary to suit the application. These reagent embodiments require only one parameter (antibiotic quantity or antibiotic to marker proportion) to be known accurately, thus minimizing the cost of manufacturing the sensible reagent and consequently the overall method.

The marker may be any material that: 1) has an identifiable signal with a magnitude proportional to the concentration of the marker; 2) has a signal that is distinguishable from other elements within the test sample; 3) has a signal and signal magnitude that are not adversely affected by growth of the target microorganism; 4) does not substantially adversely effect growth of the target microorganism; 5) does not unpredictably or adversely affect the action of the antibiotic being evaluated; and 6) one which, if necessary, will co-diffuse with the antibiotic in the growth medium during the incubation period in a predictable manner so that the local marker concentration is proportional to the local antibiotic concentration. For example, a fluorescent marker having excitation or emission wavelengths outside the range of the excitation or emission wavelengths of the growth medium, and one that does not bind to the growth medium or the target microorganism may be used. The marker and the antibiotic preferably diffuse within the growth medium at the same rate, although a similar diffusion rate is not required. A marker and an antibiotic having different, but known, diffusion rates may be used alternatively. In another example, an identifiable dye that is absorbed by the antibiotic may be used. The magnitude of the marker signal emitted from the dye is proportional to the concentration of antibiotic since it is the antibiotic that is "carrying" the dye. The terms "proportion" and "proportional" as used within the present specification comprise any relationship that can be mathematically described; e.g., x:y, x:y$^2$, x: 1/y, etc.

The present invention method includes the further steps of: a) incorporating the sensible reagent into the growth medium; b) inoculating the growth medium with the target microorganism; c) incubating the inoculated growth medium; d) determining a growth boundary of target microorganism growth; e) measuring the magnitude of the marker signal at the growth boundary; and f) determining the MIC of the antibiotic using the measured magnitude of the marker signal.

The sensible reagent is incorporated into the growth medium in a manner such that at least one gradient of reagent concentration forms within the growth medium. At one end of the gradient the antibiotic and marker concentrations are greater than those possible for the MIC of the antibiotic. At the other end of the gradient, the antibiotic and marker concentrations are less than those possible for the MIC of the antibiotic. Incorporation can be accomplished directly by inserting the reagent into the growth medium or by applying the reagent onto a surface of the growth medium. Incorporation can also be accomplished indirectly by applying the reagent onto a substrate and placing the substrate in contact with, or in close proximity to, the growth medium.

The growth medium can be inoculated by any known method acceptable for use with the growth medium and the target microorganism. The number of target microorganism microbes inoculated into the growth medium should be sufficient to provide adequate coverage over the entire area of the growth medium incorporating the reagent. The sufficiency of inoculum concentration will depend on the parameters of the MIC test at hand, including the type growth medium, target microorganism, antibiotic etc. In most cases, however, an adequate target microorganism inoculum concentration will fall between one thousand microbes per milliliter of inoculum ($10^3$ microbes/ml) and one hundred million microbes per milliliter of inoculum ($10^8$ microbes/ml); higher inoculum concentrations generally require lower inoculum volumes. As stated earlier, the target microorganism is preferably a constituent within a liquid or gel solution.

The growth medium, incorporated with the reagent and inoculated with the target microorganism, can be incubated under any conditions that are acceptable to the growth medium and the target microorganism. The growth medium is typically incubated until a section of growth medium has detectable target microorganism growth. The section of growth medium having detectable target microorganism growth will be contiguous with a section of growth medium having substantially no detectable target microorganism growth. In some instances, the section of growth medium having "substantially no" detectable target microorganism growth may have a negligible amount of target microorganism growth present. The border between the two sections is referred to as the growth boundary. The section of growth medium having detectable growth of target microorganism is that in which the target microorganism's growth is substantially uninhibited by the antibiotic. In contrast, the section having no detectable growth is that in which the target microorganism's growth is substantially inhibited by the antibiotic. The growth boundary coincides with the MIC of the antibiotic for the target microorganism being evaluated.

The position of the growth boundary is usually determined by optical means. A second method for determining the position of the growth boundary uses a marker (which may be the same as, or independent of, the marker contained within the reagent) that interacts with, including but not limited to being metabolized by, the growing microorganism to produce a sensible product. The sensible product, which is present with the target microorganism growth, is sensed to establish the growth boundary. A third method for determining the position of the growth boundary includes evaluating the light scattering characteristics within the section(s) bearing target microorganism growth versus the light scattering characteristics in the section(s) bearing substantially no target microorganism growth. In all three methods, once the growth boundary is determined, the signal from the marker within the reagent can be sensed and its magnitude measured.

The marker mixed with the antibiotic in the sensible reagent provides the quantitative information at the growth boundary that enables the MIC of the antibiotic to be calculated. Specifically, the magnitude of the marker signal at the growth boundary is proportional the marker concentration, and the concentration of the antibiotic can be determined using the known proportional relationship between the concentrations of marker and antibiotic. The exact method for determining the antibiotic concentration will depend on the physical embodiments of the growth medium, how the sensible reagent is distributed, the proportional relationship between the marker and the antibiotic within the reagent, etc. The following examples illustrate how the antibiotic concentration may be calculated using the present invention method.

EXAMPLE I

Referring to FIG. 1, in a first example the present invention method uses a Kirby-Bauer type apparatus 10 (shown in diagrammatic cross-section) which includes a plate 12, a layer of microorganism growth medium 14 of uniform thickness "T" inoculated with a target microorganism, and a disk 16. The sensible reagent 17 (with an accurately known quantity of antibiotic mixed with an imprecisely measured quantity of fluorescent marker) is applied to the disk 16 and the disk 16 is placed in contact with the growth medium 14. The sensible reagent 17 diffuses into the growth medium 14, creating a concentration gradient 18 as it travels radially (shown diagrammatically in FIG. 1). The inoculated growth medium 14 is incubated and a section 20 having detectable target microorganism growth 22 develops contiguous with a section 24 having no detectable target microorganism growth.

Figure 2:
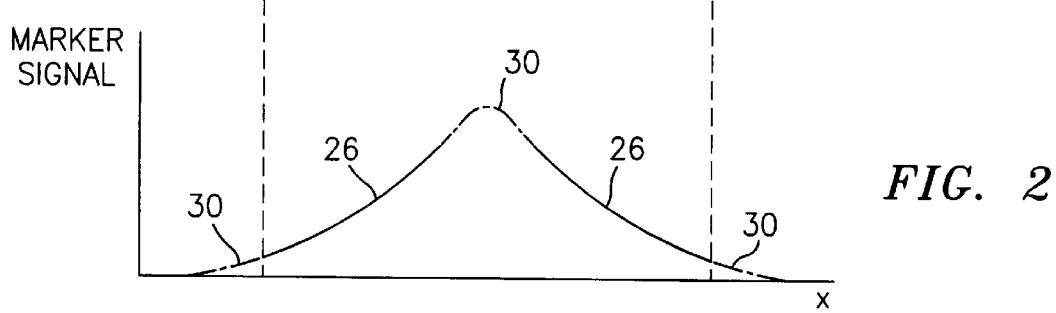
FIG. 2 is a graph depicting marker signal magnitude as a function of linear distance, associated with the Kirby-Bauer type apparatus shown in FIG. 1.

Referring to FIGS. 1 and 2, the plate 12 is placed in a commercially available scanning fluorometer (not shown) adjusted to sense the fluorescent signal characteristic of the marker. The fluorometer generates a curve 26 (FIG. 2) representing signal magnitude as a function of radial distance across the plate 12. Marker signal magnitude is a function of the marker concentration in a given volume (V), and is determined by sensing an area (A) of the growth medium 14 which has a uniform thickness (T; V=A*T). The marker signal magnitude at the growth boundary 28 between the sections 20,24, for example, is given as the signal magnitude measured within a volume (V) of growth medium 14 located at the growth boundary 28. As stated earlier, the position of the growth boundary 28 between the sections 20,24 may be determined optically, or by other means. In the growth medium 14 below the disk 16 and the section 20 of growth medium 14 having detectable target microorganism growth 22, the signal from the marker may be obscured by interference. The total signal magnitude from the marker can be determined by estimating the marker signal magnitude in the obscured regions with a curve fitting mathematical analysis. For illustrative purposes, FIG. 2 shows an example of a mathematically fit curve 30 in the obscured regions. The total signal magnitude from the marker is subsequently determined by integrating the area under the curve 26,30. As described above, the marker signal is scanned in a linear manner across the center of the test area. Since the sensible reagent 17 actually diffuses in a radial manner, it may be necessary to adjust the signal integration to reflect the radial diffusion of the reagent. The signal integration adjustment may be avoided, however, by scanning the entire area containing the radial diffusion of reagent.

The concentration of marker in the given volume (V) at the growth boundary 28 can be expressed as the ratio of the magnitude of the marker signal at the growth boundary 28 (sensed from volume V) over the total magnitude of the marker signal sensed within the total volume of the growth medium 14. The concentration of marker at the growth boundary 28, in turn, is related to the concentration of the antibiotic at the growth boundary 28 (in the same volume V), by the ratio of diffusion rates of the marker and antibiotic. If the diffusion rates are equal, the antibiotic concentration at the growth boundary 28 (i.e., the MIC of the antibiotic for the target microorganism) can be determined as follows:

$$\frac{[(\text{mag. of signal})/(V)]_{gb}}{[(\text{mag. of signal})/(\text{total volume})]_{tot}} = \frac{[(\text{am't of antibiotic})/(V)]_{gb}}{[(\text{am't of antibiotic})/(\text{total volume})]_{tot}}$$

which can be rearranged to solve for the unknown antibiotic concentration at the growth boundary 28:

$$\frac{[(\text{mag. of signal})/(V)]_{gb} * [(\text{am't of antibiotic})/(\text{total volume})]_{tot}}{[(\text{mag. of signal})/(\text{total volume})]_{tot}} = [(\text{am't of antibiotic})/(V)]_{gb}$$

If the diffusion rates of the antibiotic and marker differ, a correction factor representing the mathematical relationship between the two diffusion rates is used to correct for the difference. In addition, the above expressions require that the quantity of antibiotic in the total volume of growth medium be accurately known. If all of the sensible reagent 17 (containing an accurately known quantity of antibiotic mixed with an imprecisely measured quantity of fluorescent marker) is incorporated into the growth medium, then the quantity of antibiotic is ascertainable from the reagent. Other methods of accurately determining the quantity of antibiotic within the total volume of growth medium may be used alternatively.

EXAMPLE II

Figure 3:
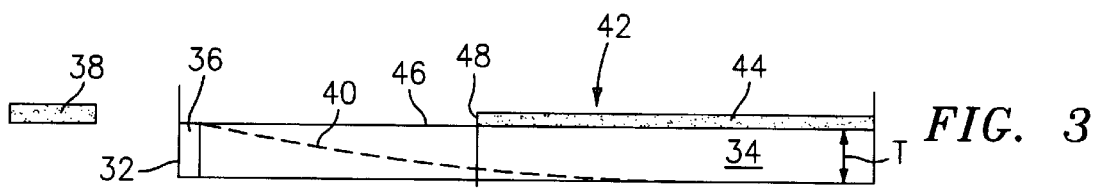
FIG. 3 shows a diagrammatic cross-section of a trough containing a microorganism growth medium to illustrate the present invention method.
Figure 4:
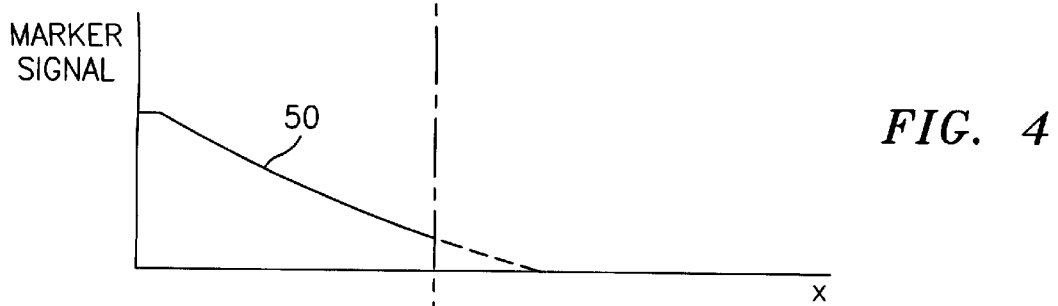
FIG. 4 is a graph depicting marker signal magnitude as a function of linear distance, associated with the apparatus shown in FIG. 3.
Figure 5:
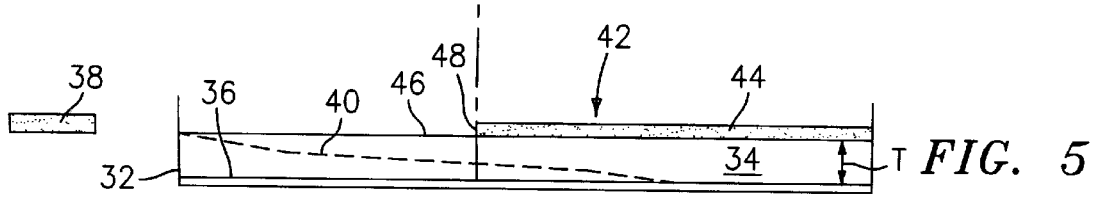
FIG. 5 shows the diagrammatic cross-section shown in FIG. 3, further including sensible reagent applied to a substrate.

Referring to FIGS. 3–5, a trough 32 contains a layer of microorganism growth medium 34 of known uniform thickness "T" inoculated with a target microorganism. FIG. 3 illustrates an embodiment where a quantity of sensible reagent 36 containing a known accurate concentration ratio of antibiotic and marker is applied to a surface of the growth medium 34 located at one end of the trough 32. FIG. 5 illustrates an alternative embodiment where a quantity of sensible reagent 36 containing a known accurate concentration ratio of antibiotic and marker is applied to a substrate 33 placed in contact with a surface of the growth medium 34 at one end of the trough 32. In both embodiments, the ratio of antibiotic to marker initial concentrations is chosen to ensure that the antibiotic and the marker will diffuse into the growth medium sufficiently enough so as to provide a readily detectable quantity of marker at the probable MIC point. The ratio of initial concentrations is expressed as the constant "$k_1$":

$$k_1 = (\text{antibiotic concentration})_{initial}/(\text{marker concentration})_{initial}$$

An accurate value representing the ratio of antibiotic to marker initial concentrations is determined at the time the sensible reagent 36 is manufactured. A reference pad 38, independent of the layer of growth medium 34, is provided containing a known amount of marker which emits a known magnitude of fluorescent signal. The marker contained within the reference pad 38 can be different from that used within the reagent 36. If the markers are different, however, or if the response of the marker within the reference pad 38 differs from the response of the marker in the growth medium 34, the concentration to signal magnitude ratio of each marker must be known:

The sensible reagent 36 diffuses into the growth medium 34, creating a gradient 40 of decreasing concentration as it travels laterally (shown diagrammatically in FIG. 3). The inoculated growth medium 34 is incubated and a section 42 having detectable target microorganism growth 44 develops contiguous with a section 46 having no detectable target microorganism growth. A commercially available scanning fluorometer (not shown) adjusted to sense the fluorescent signal characteristic of the marker is used to measure the magnitude of the marker signal emitted from a given volume (V) located at the growth boundary 48 between the sections 42,46, where the volume (V) is defined as an area (A) of inoculated growth medium 34 scanned, having a uniform thickness (T; V=A*T). As stated earlier, the position of the growth boundary 28 between the sections 42,46 may be determined optically, or by other means. The fluorometer generates a curve 50 (FIG. 4) representing signal magnitude as a function of lateral distance across the trough 32.

The concentration of the antibiotic at the growth boundary 48 (i.e., the MIC of the antibiotic for the target microorganism) can be calculated by first determining the marker concentration in a given volume (V) at the growth boundary 48 using the following relationship:

$$\frac{[\text{am't of marker}]_{ref}}{[\text{mag. of signal}]_{ref}} = \frac{[(\text{am't of marker})/(V)]_{gb}}{[(\text{mag. of signal})/(V)]_{gb}}$$

which can be rearranged to solve for the unknown marker concentration since the marker signal at the growth boundary 48 is known:

$$\frac{[\text{am't. of marker}]_{ref} * [(\text{mag. of signal})/(V)]_{gb}}{[\text{mag. of signal}]_{ref}} = [(\text{am't of marker})/(V)]_{gb}$$

Once the marker concentration at the growth boundary 48 is determined, the antibiotic concentration at the growth boundary 48 can be determined by multiplying the ratio ($k_1$) of antibiotic and marker initial concentrations times the marker concentration at the growth boundary 48, provided the antibiotic and the marker within the sensible reagent 36 have equal diffusion rates:

$$k_1 * [(\text{am't of marker})/(V)]_{gb} = \text{Antibiotic concentration at the growth boundary}$$

If the diffusion rates of the antibiotic and marker differ, a correction factor representing the mathematical relationship between the two diffusion rates is used to correct for the difference.

Although this invention has been shown and described with respect to the detailed embodiments thereof, it will be understood by those skilled in the art that various changes in form and detail thereof may be made without departing from the spirit and the scope of the invention.

I claim:

1. The method for determining the minimum inhibitory concentration of an antibiotic for a target microorganism, comprising the steps of:

(a) providing a microorganism growth medium;
   (b) providing a sensible reagent, which includes an antibiotic mixed with a first marker, said first marker having a first signal with a magnitude proportional to said first marker's concentration;
   (c) incorporating said reagent into said growth medium, in a manner that creates a gradient of concentrations of said antibiotic and said first marker within said growth medium;
   (d) inoculating said growth medium with said target microorganism;
   (e) incubating said inoculated growth medium for a period of time sufficient for said target microorganism to grow a detectable amount on a first section of said growth medium;
   (f) determining a growth boundary between said first section of said growth medium having detectable target microorganism growth and a second section of said growth medium having substantially no detectable target microorganism growth; and
   (g) measuring said magnitude of said first signal at said growth boundary; and
   (h) determining said minimum inhibitory concentration of said antibiotic using said measured magnitude of said first signal.

2. The method according to claim 1, wherein said inoculating step comprises providing said target microorganism in a liquid solution, wherein said liquid solution hydrates an initially dehydrated said growth medium during said inoculating step.

3. The method according to claim 2, wherein said incorporating step includes inserting said sensible reagent directly into said growth medium.

4. The method according to claim 1, wherein said incorporating step includes applying said sensible reagent directly onto a surface of said growth medium.

5. The method according to claim 1, wherein said incorporating step includes applying said sensible reagent onto a substrate and placing said substrate in contact with, or in close proximity to, said growth medium.

6. The method according to claim 1, further comprising the steps of:

providing a second marker, wherein said second marker interacts with said detectable target microorganism growth to produce a sensible second signal;
   sensing said second marker to establish said growth boundary.

7. The method according to claim 1, further comprising the steps of:

sensing said growth medium for contiguous regions having differences in light scattering characteristics;
   determining said growth boundary along a border between said contiguous regions.

8. The method according to claim 1, wherein said step of providing said sensible reagent further comprises:

providing said antibiotic in an accurate known quantity mixed with a useful quantity of said marker.

9. The method according to claim 8, wherein said measuring step further comprises measuring said magnitude of said first signal within a known volume of said growth medium, said volume located at said growth boundary.

10. The method according to claim 9, further comprising the step of measuring a total magnitude of said first signal within said growth medium.

11. The method according to claim 10, wherein said determining said minimum inhibitory concentration step further comprises the step of:

multiplying said accurate known quantity of antibiotic times a ratio of said magnitude of said first signal measured within said known volume over said total magnitude of said first signal measured within said growth medium;
    wherein said product of said multiplying step equals said minimum inhibitory concentration of said antibiotic for said target microorganism.

12. The method according to claim 1, wherein said step of providing said sensible reagent further comprises:

providing said antibiotic and said first marker in known accurate proportion, wherein said accurate proportion may be mathematically represented as a ratio of an initial antibiotic concentration over an initial marker concentration.

13. The method according to claim 12, further comprising the step of:

providing a reference pad containing a known quantity of a reference marker, said first quantity of reference marker having a known magnitude of reference signal.

14. The method according to claim 13, wherein said measuring step further comprises measuring said magnitude of said first signal within a known volume of said growth medium, said volume located at said growth boundary.

15. The method according to claim 14, wherein said determining said minimum inhibitory concentration step further comprises the steps of:

multiplying said magnitude of said first signal measured within said known volume times a ratio of said known quantity of said reference marker over said known magnitude of said reference signal, and times said ratio of said initial antibiotic concentration over said initial marker concentration;
    wherein said product of said multiplying step equals said minimum inhibitory concentration of said antibiotic for said target microorganism.

16. The method for determining the minimum inhibitory concentration of an antibiotic for a target microorganism, comprising the steps of:

(a) providing a microorganism growth medium;
    (b) providing a sensible reagent, which includes an antibiotic mixed with a marker, said marker having a signal with a magnitude which is proportional to said marker's concentration;
    (c) incorporating said reagent into said growth medium, in a manner that creates a gradient of concentrations of said antibiotic and said marker within said growth medium;
    (d) inoculating said growth medium with said target microorganism;
    (e) incubating said inoculated growth medium for a period of time sufficient for said target microorganism to grow a detectable amount in a first section of said growth medium, said first section having a concentration of said antibiotic insufficient to inhibit growth of said target microorganism on said growth medium, said first section contiguous with a second section of said growth medium bearing substantially no detectable amount of target microorganism growth, said second section having a concentration of said antibiotic sufficient to substantially inhibit said target microorganism growth;

(f) determining a growth boundary between said first section of said growth medium having detectable target microorganism growth and said second section of said growth medium having substantially no detectable target microorganism growth; and (g) measuring said magnitude of said marker signal at said growth boundary; and (h) calculating said minimum inhibitory concentration of said antibiotic using said measured magnitude of said marker signal.

17. A method for determining the minimum inhibitory concentration of one or more antibiotics for a target microorganism, said method using a microorganism growth medium and a sensible reagent, said sensible reagent including an antibiotic mixed with a marker, said marker having a signal with a magnitude proportional to said marker's concentration, wherein said reagent is incorporated into said growth medium in a manner that creates a gradient of concentrations of said antibiotic and said marker within said growth medium, said method comprising the steps of:

(a) inoculating said growth medium with said target microorganism;

(b) incubating said inoculated growth medium for a period of time sufficient for said target microorganism to grow a detectable amount on a first section of said growth medium;

(c) determining a growth boundary between said first section of said growth medium having detectable target microorganism growth and a second section of said growth medium having substantially no detectable target microorganism growth; and (d) measuring said magnitude of said marker signal at said growth boundary; and (e) determining said minimum inhibitory concentration of said antibiotic using said measured magnitude of said marker signal.

18. The method for determining the minimum inhibitory concentration of an antibiotic for a target microorganism, comprising the steps of:

(a) providing a microorganism growth medium, which includes a sensible reagent;

(b) inoculating said growth medium with said target microorganism;

(c) incubating said inoculated growth medium for a period of time sufficient for said target microorganism to grow a detectable amount on a first section of said growth medium;

(d) determining a growth boundary between said first section of said growth medium having detectable target microorganism growth and a second section of said growth medium having substantially no detectable target microorganism growth; and (e) sensing said sensible reagent at said growth boundary; and (f) calculating said minimum inhibitory concentration of said antibiotic using said sensed sensible reagent.

19. An apparatus for determining the minimum inhibitory concentration of antibiotic for a target microorganism sample, comprising:

a sample holder;

a sheet of microorganism growth medium disposed in said sample holder; and a sensible reagent which includes an antibiotic and a marker, said marker having a signal with a magnitude proportional to said marker's concentration, said reagent incorporated into said sheet of growth medium in a manner that creates a gradient of concentrations of said antibiotic and said marker within said growth medium.

20. An apparatus according to claim 19, further comprising:

a sensor for sensing for said marker signal; and means for detecting target microorganism growth;

wherein said sensor is operable to sense for said marker signal at a growth boundary detected contiguous with said target microorganism growth.

* * * * *